United States Patent
Jin et al.

(10) Patent No.: US 8,443,681 B2
(45) Date of Patent: May 21, 2013

(54) METHOD AND APPARATUS FOR VISUALIZING CONTRACTION STRESS FROM CURABLE MATERIALS

(75) Inventors: Xiaoming Jin, Middletown, DE (US); Louis Bertrand, Lewes, DE (US); Qizhou Dai, Dover, DE (US); Bill Martin, Lewes, DE (US); Nils Classen, Middletown, DE (US); Nikki Sparacino, Harrington, DE (US)

(73) Assignee: DENTSPLY International Inc., York, PA (US)

( * ) Notice: Subject to any disclaimer, the term of this patent is extended or adjusted under 35 U.S.C. 154(b) by 64 days.

(21) Appl. No.: 13/290,512

(22) Filed: Nov. 7, 2011

(65) Prior Publication Data
US 2012/0285258 A1 Nov. 15, 2012

Related U.S. Application Data (60) Provisional application No. 61/411,686, filed on Nov. 9, 2010.

(51) Int. Cl.
*G01N 3/02* (2006.01)
(52) U.S. Cl.
USPC .............................. 73/856; 73/762

(58) Field of Classification Search
USPC .................. 73/856, 54.21, 54.28, 54.39, 762, 73/783, 789
See application file for complete search history.

(56) References Cited

U.S. PATENT DOCUMENTS

| | | | | |
|---|---|---|---|---|
| 4,837,776 | A * | 6/1989 | Poll | 374/56 |
| 5,487,307 | A * | 1/1996 | Landgren et al. | 73/803 |
| 6,523,397 | B1 * | 2/2003 | Tosaki | 73/54.39 |
| 6,871,550 | B2 | 3/2005 | Eichmiller | |
| 7,544,721 | B2 | 6/2009 | Jin et al. | |

FOREIGN PATENT DOCUMENTS

FR 2787088 * 6/2000

* cited by examiner

*Primary Examiner* — J M Saint Surin
(74) *Attorney, Agent, or Firm* — Leana Levin; Douglas J. Hura; David A. Zdurne

(57) ABSTRACT

Disclosed herein is an apparatus and a method to use such an apparatus for visualizing the contraction stress from curable materials. Particularly, a simple test device has been designed and fabricated and a method of using such a device, which allows a user to easily distinguish the curable materials that can generate contraction stress in different magnitudes. More specifically, the present disclosure provides a simple and effective way to make the complicated contraction stress due to polymerization (curing or setting) visualizable and audible.

12 Claims, 6 Drawing Sheets

Side View
Step 1
Cure Sample

Side View
Step 1
Cure Sample

FIG. 1

Top View
Step 2
Start Timer

FIG. 2

Top View
Step 3
Note Time
Coverslip Cracks

METHOD AND APPARATUS FOR VISUALIZING CONTRACTION STRESS FROM CURABLE MATERIALS

This application claims the benefit of Provisional Application No. 61/411,686, filed Nov. 9, 2010.

The present disclosure relates to a test method and a test apparatus. More specifically, a simple method and a test device is designed and fabricated, which allows one to easily distinguish when a curable material has lower contraction stress. This is apparent when a curable material having a higher contraction stress may cause one component of the test apparatus, such as a cover slip or cover glass, to be cracked or to completely break apart. In contrast, when a similar test is undertaken with a curable material having a lower contraction stress the same component of the test apparatus remains intact.

BACKGROUND

There has been tremendous effort in restorative dentistry to investigate the effect of shrinkage and stress of a dental composite on the longevity of a tooth restoration. Theoretically, either lower shrinkage or lower stress should be helpful in minimizing the failure in tooth restoration. However, such a statement might not be true in reality because of the complex nature of tooth restorations which involve not only the restorative material, such as a low shrink or low stress composite, but also involve tooth cavity preparation, adhesive application, composite placement, and curing process/efficiency, and the like. All of these factors are highly dependent on how a clinician understands and masters the dental material and the restoration procedure.

The origin of stress from a composite in adhesive restorations is attributed to the restrained shrinkage, which is a direct result of a curing or polymerization process and is highly dependent on the configuration of the restoration. In addition, the non-homogeneous deformations during functional loading can promote and/or damage the restored tooth, the interface as well as the coherence of the composite or the composite itself. Certainly, the damage from shrinkage or contraction stresses can be reduced by application of an elastic lining at the adhesive interfaces and by slowing the initial curing process.

Unfortunately, it is part of such a complicated process that makes the lack of a convincing clinical study about the correlation between polymerization shrinkage and stress and the longevity of a restored tooth. One primary reason for the difficulty in such a study is caused by the lack of a standard test methodology for effective measurement of shrinkage and/or stress.

There are test methods for polymerization shrinkage as well, which could be classified in two categories: (1) measuring directly by the dimensional change and (2) measuring indirectly by the density change.

1. Archimedes' or buoyancy method: the density of the a material is measured before and after curing by water Pycnometer and a buoyancy balance. Then the difference is calculated to generate the total volume shrinkage at a given measurement time.
    Advantages are that the method is simple, easy, quick.
    Disadvantages are that the method is rough, inaccurate, no shrinkage kinetic, liquid or sticky or moisture sensitive materials can be tested, porosity in sample demonstrates significant effect on the results.
2. Water or Mercury dilatometer equipped with LVDT (Linear Variable Differential Transducers) allows for the direct measurement of the replacement of any volume during and/or after curing.
    Advantages are that the method is accurate and that shrinkage kinetics and absolute volume shrinkage can be measured.
    Disadvantage are that the method takes time and may consume materials sensitive, and work with liquid or sticky materials or moisture-sensitive materials is not possible in water dilatometer case. Shrinkage is dependent on the given time, curing intensity and duration.
3. Watts method is where the linear displacement of the bent thin glass or plastic cover caused by shrinkage is registered by LVDT or micrometer during/after curing, and then volume shrinkage is calculated according to a formula with the assumption of uniform shrinking.
    Advantages of the method are shrinkage kinetic small sample, and sticky sample are acceptable for measurement.
    Disadvantages of the method are that the early stage is less sensitive so it is less accurate, the method is sample size dependent, and also light intensity and curing time dependent.
4. Zurich method is similar to the Watts method, but the movement of a metal plate is registered by an infrared ("IR") beam.
    Advantages of the method are that it is accurate, small samples are acceptable, and sticky samples are acceptable.
5. CCD/Image method includes high resolution CCD (Charged-coupled Device) video image that is recorded and analyzed before and after curing.
    Advantages if this method include direct absolute volume shrinkage determination, and that there is no heat effect on any size as long as the sample is fully cured.
    Disadvantages of the method include a decrease in accuracy due to the image resolution, and a shrink kinetic defect within sample may be possible.
6. Gas Pycnometer measures direct volume replacement by inert gas that is registered before and after curing.
    Advantages of this method are that it is quick, easy, any materials can be measured, long term shrinkage can be measured and temperature does not significantly impact the measurement.
    Disadvantages include no shrinkage kinetic, too sensitive due to the extreme penetration capability or helium gas.
7. Strain Gauge method may be considered a stress test method due to its nature in monitoring post-gel polymerization contraction by the change of strain of a known modulus material that is directly contacted with the specimen.
    Advantages are that the method is easy and quick.
    Disadvantage is that only post polymerization shrinkage is recorded.
8. Micrometer method includes measurement of macroscopic dimensional change that is recorded by a micrometer before and after curing.
    Advantages are that the method is easy and quick.
    Disadvantages are that the method is inaccurate and too rough.

In addition, more attention recently has been focused on polymerization (or contraction) stress because there is actually no linear correlation between polymerization shrinkage and polymerization stress within any curable system. The total contraction stress does not depend only on how much the material shrinks it also kinetically depends on the evolving elastic modulus ("stiffness") of such curable material upon curing. Furthermore, the overall curing stress trapped within in the cured material also depends upon the constrained environment (the shape of the cavity), the established bonding between the cured material and its substitute (the tooth). Contraction stresses from polymerization contraction or polymerization shrinkage in composite restorations is able to deform a restored tooth. This may be reflected as de-bonding, micro-leakage, enamel/dentin cracking, and/or post-operative sensitivity. It also should be pointed out that the contraction stress only becomes a severe issue when the materials are used in well-bonded cases. In other words, only under increasingly constrained conditions, such as heavily bonded posterior restoration, extra attention should be paid to stress.

"Curing Stress" is used herein to refer to the stress developed in an adhesive restoration process instead of "shrinkage stress" or "polymerization stress" for the following reasons.
1) "Curing" or "setting" is commonly used to described the polymerization process involving cross-linking and the polymerization process involved in adhesive restoration is a cross-linking process.
2) Though such a stress is originated from contraction or shrink due to polymerization, not all of polymerization or its contraction (shrink) will contribute to the stress that would cause a clinical problem or sever damage to a restored tooth.
3) In a non-crosslinking (linear or branching) polymerization process, much less contraction (shrink) is converted into stress due to the less restricted nature (high chain mobility) of the formed polymers.
4) In a cross-linking polymerization process more contraction (or shrink) is converted to stress due to the increasing difficulty of chain mobility (highly restricted), which can result in trapped stress within a cured system.
5) Polymerization shrinkage is not necessarily linearly related to the curing stress.
6) In an adhesive restoration cases, additional restriction occurs in the curing composite, that is bonding to the surrounding tooth. The more bonding surface (higher C-factor), the more restriction, which is the reason that low curing stress would matter more in posterior restorations than in an anterior restorations. Of course, reduced curing stress would always be welcomed by any anterior application as well.
7) In posterior restorations with current adhesive composites there is an increased restriction, which is not good for reducing the impact of curing stress, but the curing stress could be reflected in different ways, depending upon its compatibility with (or relation to) the bonding system.
   If the rate of development of the trapped stress within the curing composite is faster than the rate of bonding strength to bond composite to the tooth (dentin/enamel), an interfacial gap may be formed. In this case, future tooth cracks might be effectively avoided.
   If the rate of composite polymerization is too slow than the bonding between the composite and a tooth (dentin/enamel), then cracks within the cured composite may occur. In this case, future cracks within tooth could also be avoided.
   If good cure with the composite and excellent bond between such cured composite and tooth (dentin/enamel) are achieved (for most cases in current adhesive restorations), the impact of the trapped curing stress on the restored tooth will be strengthened because of the increasing restriction. An increase in tooth cracks and sensitivity may result.

Therefore, to a restored tooth the curing stress is just a dynamic reflection to a delicate balance between molecular contraction (shrinkage) and network formation (modulus) in a well-bonded system through entire curing process. It is believed that the curing stress generated by constrained shrinkage is more harmful clinically than that from an unconstrained shrinkage. In another word, curing stress becomes ISSUE only due to a constrained restoration, in which polymerization shrinkage would be more effectively converted into the "deadly" force. Under less constrained condition (such as anterior application), however, less clinical issue from curing stress would be resulted though same polymerization shrinkage might be involved.

There are many efforts in developing an effective test method to measure contraction stress or polymerization stress as well. For example, U.S. Pat. No. 6,871,550 discloses a method and an apparatus (tensometer) for measuring the characteristics of curing polymers, which utilizes cantilever beam technology to determine characteristics of a polymer during the curing process, including stress-related forces that developed during the polymer curing process. Such a tensometer also provide for controlling and monitoring environmental condition during the curing process. Such an apparatus helps us understand more about polymerization stress, particularly the results suggest that there is not necessarily a linear relationship between shrinkage and stress during the involvement of variable modulus of curing materials, which on the other hand allow developing new resin systems and/or formulated compositions to reduce polymerization stress other than shrinkage approach. However, unlike shrinkage, which has been well pictured by conventional wisdom as dimensional reduction or gap formation, to picture curing stress remain quite challenge.

Obviously, there is strong desire for a way to effectively relate such contraction stress to a day-to-day operation. More specifically there is need to creatively illustrate the complicated phenomena, polymerization stress, in a simple way so as to have better understanding about the possible impact of curing stress. Therefore, the primary objective of present invention is to provide a solution to such a need.

SUMMARY

The present disclosure relates to a test method and a test apparatus. More specifically, a simple method and a test device are designed and fabricated, which allow for easily distinguishing the curable materials with lower contraction stress. For example, curable material that have a higher contraction stress causes one of the components of the apparatus, a cover slip or a cover glass, to crack or to completely break apart. In contrast, curable material with lower contraction stress will allow the cover slip or cover glass to remain intact.

DESCRIPTION

In a prior art Viatman derived an equation and an experimental method to investigate the strength of glass plate, in which a square glass plate of thickness (h), resting freely on a ring support of diameter (2b) is subjected to an external load (P) applied along a concentric circle of diameter (2a). If the geometric relationships are such that the deflection of the plate is small as compared with its thickness, the deflection ($w_0$) and the stresses ($\sigma$) at the center of the plate are given by the equations:

$$w_0 = [(\eta b^2)/(8\pi D)]P \quad (1)$$

Where $$D = Eh^3/[12(1-v^2)]$$

$$\eta = 1 + [(1-v)/(1+v)][(b^2-a^2)/2C^2] - a^2/b^2[1+\ln(b/a)]$$

$$\sigma = (3/2)[(1+v)/\pi h 2)]\{\ln(b/a) + (1-v)/(1+v)[(b^2-a^2)/2c^2]\}P \quad (2)$$

However, if the deflection of the glass plate is 2-3 times greater than the thickness of the plate, a more completed equation composed of flexural and membrane components has to be employed in order to calculate the stresses in a flexible glass plate:

$$\delta = \delta_f + \delta_m$$

$$\delta_m = 0.407E(h^2/b^2)\chi^2$$

$$\delta_f = [3a(1+\delta_f)/bB]\{in(b/a)+(1-v)/(1+v)[(b^2-a^2)/2c^2]\}E(h^2/b^2)\chi$$

It was further pointed that these equations derived can also be used to estimate the strength of glass as the stress corresponding to the breaking load.

In other prior art, Watts and Cash reported a test method based on a similar thin glass deflection (bonded disk), which is constructed around a disc-shaped specimen sandwiched between one flexible thin glass plate and one rigid glass plate. The deflection of the flexible glass plate is attributed to polymerization contraction of the bonded material. Accordingly, such a deflection is measured by an LVDT transducer as a way to determine polymerization shrinkage. Sine the dimensional changes were confined to the specimen disc-thickness dimension, such that the fractional linear shrinkage approximated the volumetric shrinkage.

In addition, the flexural rigidity (D) of a plate with such a setup can also be defined by the following equation as described previously:

$$D = Eh^3/[12(1-v^2)]$$

Where E=Young's modulus (~70 GPa for soda glass), v=Poisson's ratio (~0.3).
If h=plate thickness (0.17 mm for cover slip or 1.0 mm for glass slide), then $$D = 3.15 \times 10^{-2} \text{ N m for the glass cover slip}$$

$$D = 641 \times 10^{-2} \text{ N m for the glass slide}$$

If an evenly distributed pressure (P) is applied to such a glass plate supported on a ring of radius (a), the deflection (Z) at the centre of the plate is given by the following equation:

$$Z/P = (a^4/D)(1/64 + 1/16(1+v))$$

And if a=8 mm for the radius of a supporting ring to the glass plate $$Z/P = [(0.008)^4/(3.15 \times 10^{-2})] \times 0.09688 = 12.6 \times 10^{-9} \text{ m}^3\text{N}^{-1} \text{ for cover slip and,}$$

$$Z/P = [(0.008)^4/(641 \times 10^{-2})] \times 0.09688 = 6.2 \times 10^{-11} \text{ m}^3\text{N}^{-1} \text{ for glass slide}$$

Obviously, much less pressure or force is needed so as to cause the same amount of plate deflection, or surpass its deflection limit, which eventually leads to plate cracking.

It should point out such a theoretical consideration is based on the response of single plate under pressure. For light curable material sandwiched by two glass plates, most contraction stress is concentrated onto the very first glass that is closest to the light source due to quick polymerization and immediately decreased mobility. Accordingly, more contraction deflection but less contact stress should be developed in the lower plate further away from curing light as a result of depth of cure. When a rigid glass plate is placed close to the light, more deflection would be directed to the other plate, especially if it is a flexible one. Indeed, with the Watts and Cash method, the tested specimens of light curable materials were irradiated through the rigid plate. The upper, flexible glass plate was readily deflected by an increase of the adhesive stress from the polymerizing and shrinking sample. However, any stress-related cracks within any bonded disks would not necessarily occur under such curing due to the rigidity nature of the glass plate where the initial curing started. Therefore, this setup and this method are not suitable to establish any relation with polymerization stress from the tested material, though it has been proved as an effective method to measure polymerization shrinkage.

In the present disclosure, a method and an apparatus are developed to correlate the polymerization stress to the ultimate deflection, that is, the breaking apart.

During the method to measure polymerization stress by using an ADA tensometer, it was discovered that some high stress composite can cause a quick de-bonding due to its rapid stress build-up, even sometimes resulting in the quartz rod being cracked. This is the worst case scenario during the stress measurement (a failed test). Most of the composites with moderate stress would not necessarily lead to such a broke/cracked Q-rod. This triggered our desire to develop a demonstration method for polymerization stress. Instead of a quartz rod as used in a tensometer, standard glass slides were examined first since it would allow an economic and portable demonstration. Initially it was discovered that contraction stress from certain composites is high enough to break the standard glass slides apart if proper spacers were inserted between two well-bonded slides. It should be pointed out that good bonding must be present, which basically serves the purpose of holding the curable material and glass substrates together for the maximum transformation of contraction or shrinkage into stress.

There are two folds of impacts from stress: first, the rapid stress build-up rate would compete with bonding strength development, which can cause premature de-bonding; secondly, the stress's impact can be maximized only under highly constrained conditions if an excellent bond is established, from which the impact from stress would be reflected as the cracks within the bonded surrounding or substitute. A demonstration might not necessarily cover both aspects of the impacts from the shrinkage stress. Thus, a preliminary setup was built by using two frosted glass slides (1 mm×25 mm×75 mm), stacked together, and a rigid steel spacer of 2 mm in thickness was also employed. Then curable material was placed between the two glass slides with the spacer to control the thickness. After curing from the top of one glass slide, it was set at an ambient temperature of from about 20° C. to about 26° C. As expected, the contact stress from the curable composite was high enough to break the top glass apart, though it took from about 1 hour to about 24 hours.

Furthermore, it was discovered that if a thin glass plate or cover slip were used to replace the rigid glass slide then proper surface treatment is needed with such cover slip as well, of which could be resulted from a locally frosted spot via sand-blasting and additional silane application to ensure good adhesion between the cured materials and the cover slip. Enormous cracks would occur more quickly within the cover slip than occurred with the more rigid glass slide.

Remarkably, by employing an apparatus and testing method as described herein, the disclosed apparatus can effectively distinguish between high stress material and low stress material by the formation of cracks in the cover slip during and/or post light irradiation. More importantly, this apparatus and method described herein provide a way to visibly determine the potential impact from high stress material to its bonded substitute. The following examples offer further detail about the apparatus and the method disclosed herein.

A general description of an apparatus as disclosed herein follows.

As showed in FIGS. 1, 2, 3 and 4a, 4b, 4c, the disclosed apparatus may be composed of a rigid substrate glass (1), a rigid ring-shaped spacer (2), a thin glass cover slip (3), a base or supporting bed (2) to center the glass substrate (1), a ride-on piece (7) with single or dual test well(s), and a light guide holder (8), on which the curing light (5) would sit on top of the placed curable material or specimen (4) without touching the cover slip (3).

In embodiments, the cover slip (3) suitable for the apparatus disclosed herein may have a surface treatment, such as the cover slip (3) may be frosted. Frosting the cover slip (3) entails first providing a standard cover slip (3) with thickness of from about 0.01 mm to about 0.1 mm, such as from about 0.1 mm to about 0.5 mm or from about 0.15 mm to about 0.25 mm. Covering the cover slip (3) with tape having an about 08 mm opening in the center. Gently sand-blasting the opening of the tape covered cover slip (3) to create a frosted surface. After cleaning and drying the frosted cover slip (3), additional silane solution (A-174) may be applied to the frosted area. The treated cover slip (3) may then be dried prior to use.

In alternative embodiments, a standard clean cover glass (3) may be used without further treatment, or a glass cover slip (3) having undergone any suitable treatment, such as etching or silanation, may be used.

In embodiments, a stop watch may be used to record the time elapsed before cracking of the cover slip (3) occurs. The stop watch, or any suitable time measuring device, may be started from the time the curing light is applied to the specimen (4) that has been placed under the cover slip (3).

The curable material or specimen (4) may be any suitable material such as resin, cements or composites. In embodiments, the curable material that is most suitable for use in the apparatus and method described herein is a relatively lower viscosity material having a viscosity of from about 140K Pa·s to about 40 Pa·s at a temperature of 35° C. at a shear force range of from about 10 Pa to about 20 Pa like most flowable composites, for example, that allows for sufficient contact between the curable material or specimen (4) and its two contact surfaces—the rigid substrate and the cover slip. The curable material or specimen (4) may be cured by any curing process, such as a light-initiated curing process, for example, curing by any light source such as halogen light, LED light, plasma light, etc., self curing process or a thermal curing process.

A method utilizing the disclosed apparatus is also described herein. First, the rigid substrate (1) is placed on top of the supporting bed (6). The spacer (2) is then placed on the rigid substrate (1). The thickness of the spacer suitable for use herein may be from about 0.1 mm to about 5 mm, such as from about 1 mm to about 4 mm or from about 1.5 mm to about 3 mm or from about 2 mm to about 2.5 mm. The inner diameter of the spacer may be from about 15 mm to about 25 mm and the outer diameter may be from about 20 mm to about 30 mm, such as the inner diameter being from about 18 mm to about 20 mm and the outer diameter being from about 23 mm to about 25 mm. A ride-on piece (7) having a top part is placed on top of the rigid substrate (1) and spacer (2). The curable material or specimen (4) is then placed onto a cover slip (3). The loaded cover slip (3) is then inverted and it is carefully set such that the cover slip is substantially centered on the spacer (2). Gravity is generally sufficient to ensure that the loaded cover slip (3) contacts both curable material (4) and the rigid substrate (1). If gravity is not sufficient, a gentle touch to the cover slip (3) should be sufficient to ensure that the curable material (4) is in contact with the cover slip (3) and rigid substrate (1). A light guide piece (8) is set in the well portion of the ride-on piece (7). Caution should be taken to avoid the bottom part of the ride-on piece (7) touching any part of the loaded cover slip. Finally, a curing light (5) may be activated and timer turned on to determine the length of time necessary for the curable material or specimen (4) to be cured.

EXAMPLE 1

A conventional high stress flowable composite (Supreme Flow plus) was placed and sandwiched between two pieces of frosted glass slides. Sample thicknesses were kept at about 2 mm, which was guided by two steel spacers of about 2 mm and they were kept apart in about ca. 50 mm from each other. With a 20" curing, the top slide bent downward and loaded the stress due to the spacers. After overnight setting at room temperature, about 25° C., it was found that Supreme Flow caused the top glass to break into two parts along the edge of cured specimen.

EXAMPLE 2

Using same setup and method, a low stress material (SDR) was tested. It was found that the glass slide remained intact even after several weeks post curing.

EXAMPLE 3

Figure 1:
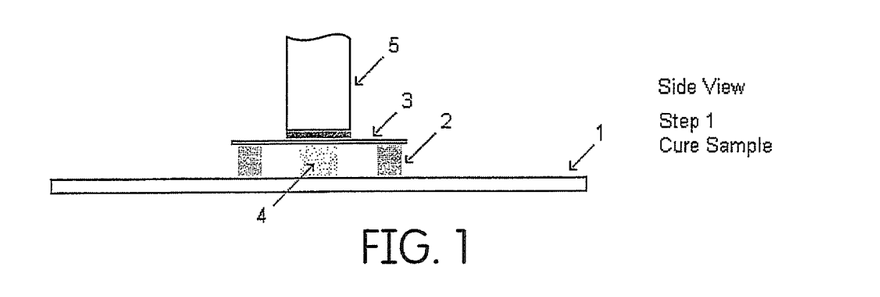
FIG. 1 shows a side view of the apparatus disclosed herein.
Figure 2:
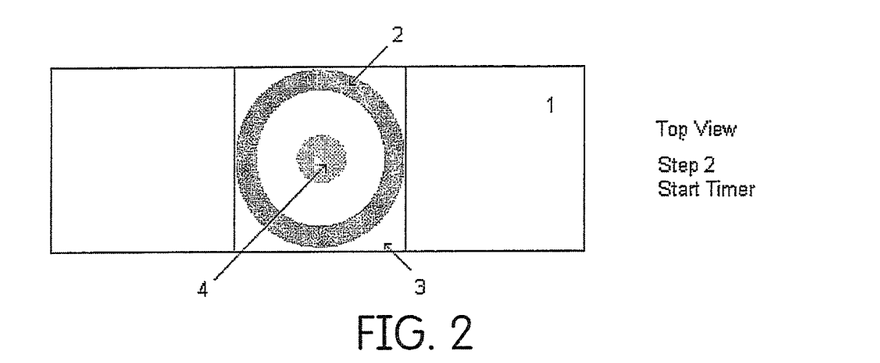
FIG. 2 shows a top view of the apparatus described herein.
Figure 3:
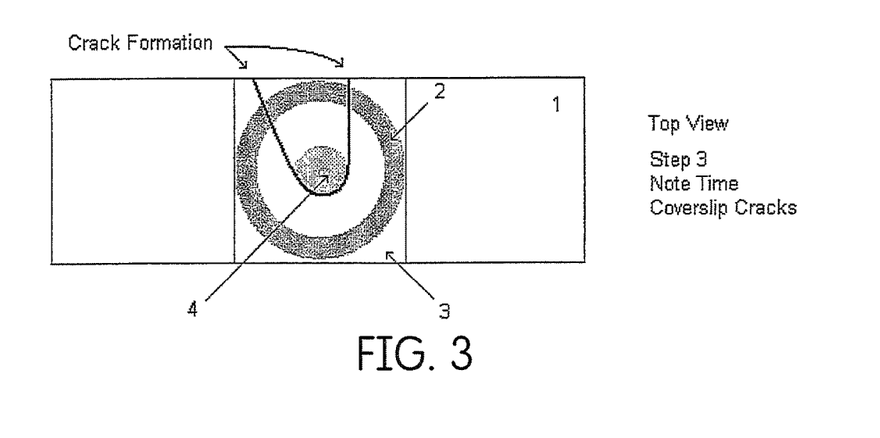
FIG. 3 shows a top view of the apparatus described herein.
Figure 4A:
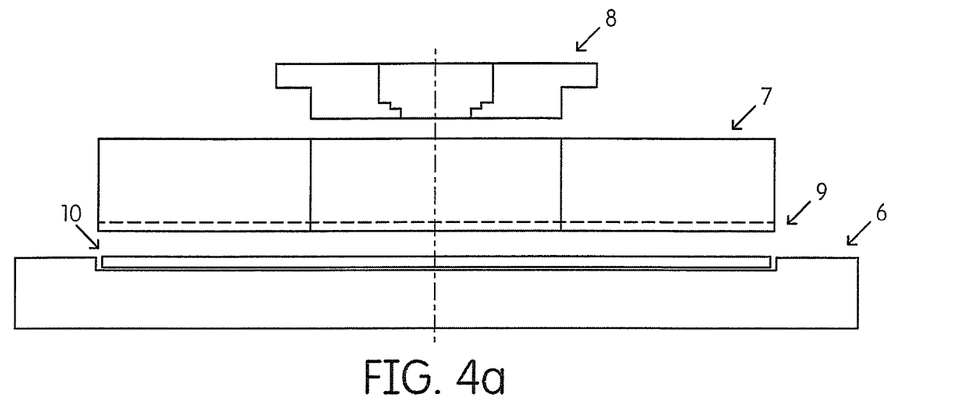
FIG. 4a shows a side view of the apparatus disclosed herein.
Figure 4B:
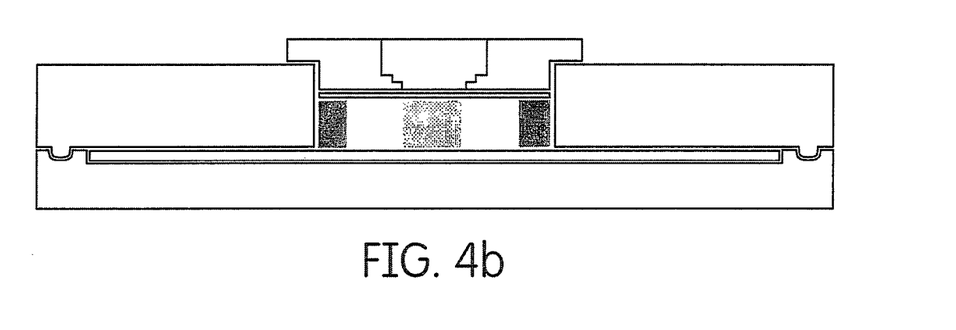
FIG. 4b shows a side view of the apparatus disclosed herein.
Figure 4C:
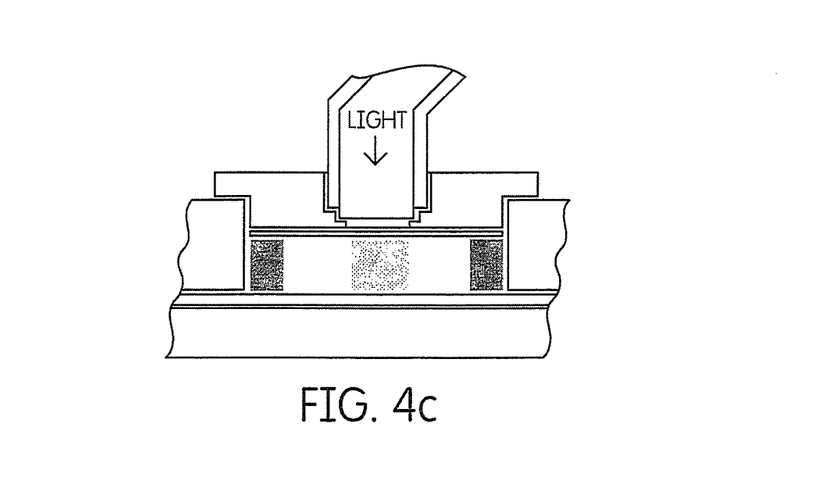
FIG. 4c shows a side view of the apparatus disclosed herein.
Figure 5A:
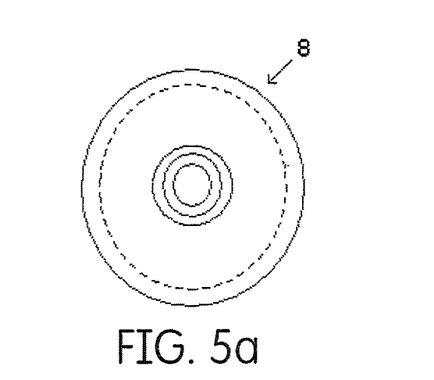
FIG. 5a shows a top view of the apparatus described herein.
Figure 5B:
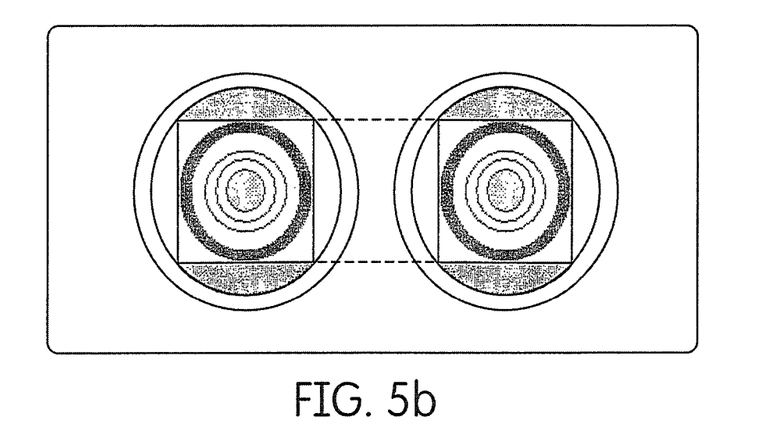
FIG. 5b shows a top view of the apparatus described herein.
Figure 5C:
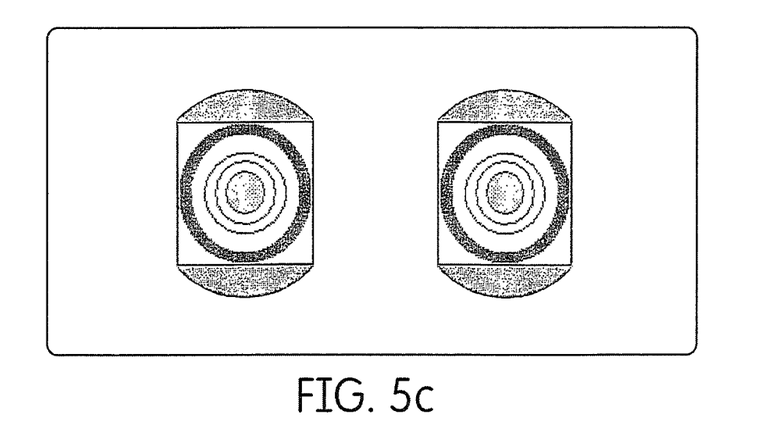
FIG. 5c shows a top view of the apparatus described herein.
Figure 5D:
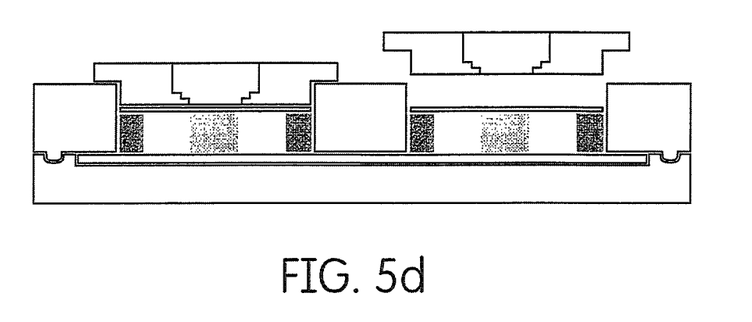
FIG. 5d shows a side view of the apparatus disclosed herein.
Figure 5E:
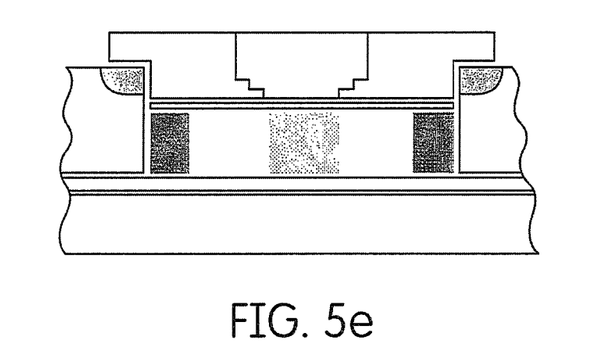
FIG. 5e shows a side view of the apparatus disclosed herein.
Figure 6A:
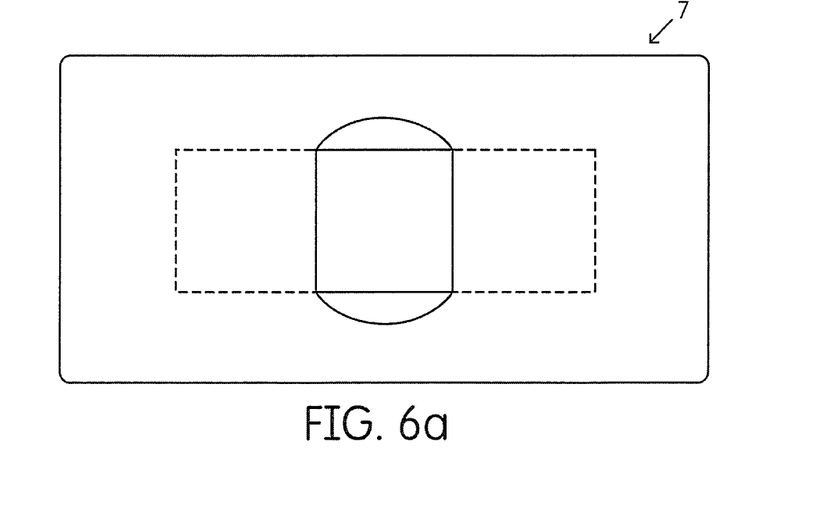
FIG. 6a shows a top view of the apparatus described herein.
Figure 6B:
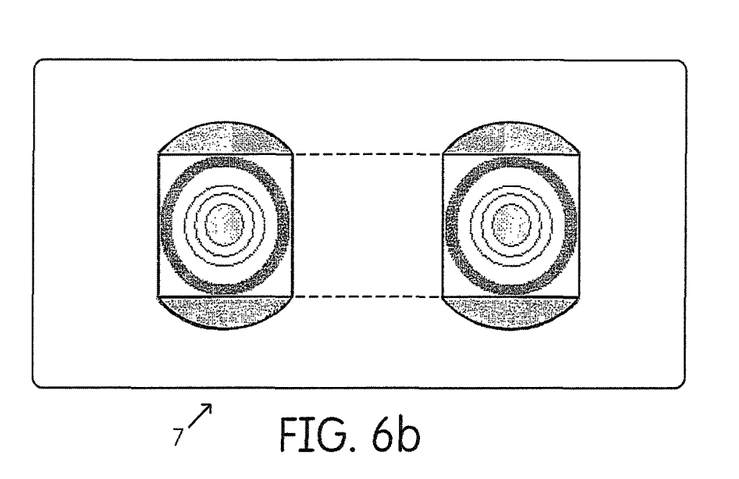
FIG. 6b shows a top view of the apparatus described herein.
Figure 7:
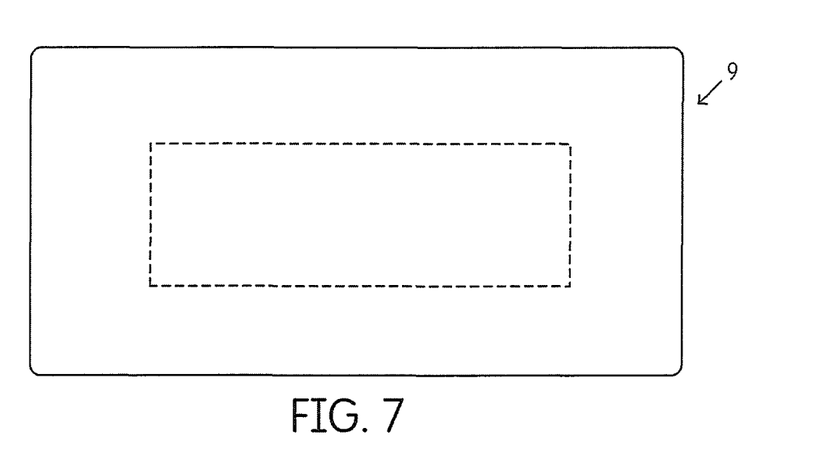
FIG. 7 shows a top view of the apparatus described herein.
Figure 8:
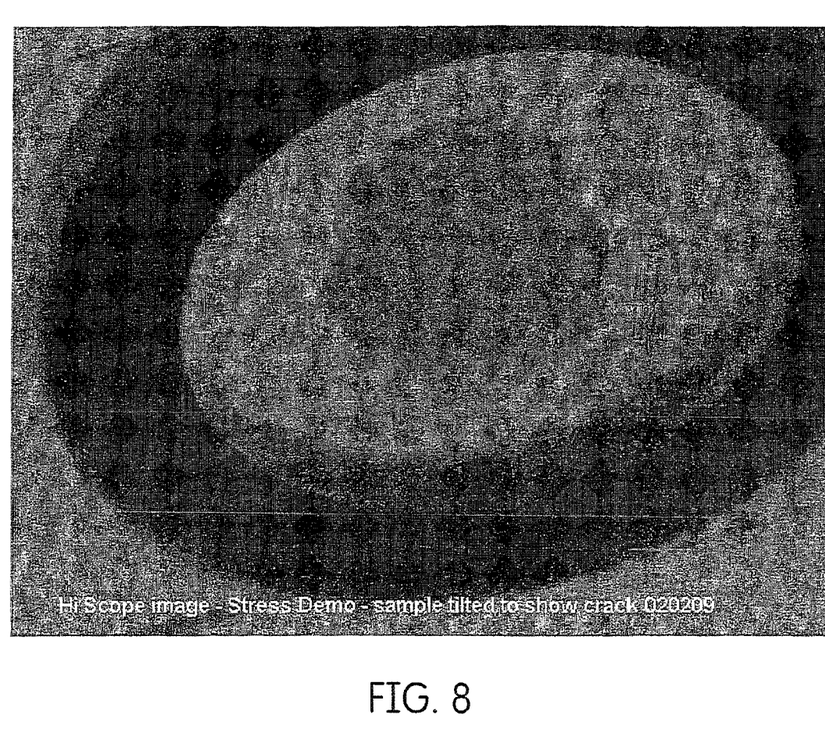
FIG. 8 shows a photograph demonstrating a crack in the cover slip of the apparatus described herein.

Using the apparatus as described above and silanated, a frosted cover slip to replace the rigid glass slide, a high stress flowable composite (Supreme Flow plus) was tested again. After the light was turned off, the time until a clear cracking occurred was measured, by which a clear sound was also accompanied. FIG. 8 shows a typical cracking seen for high stress materials.

EXAMPLE 4

Similarly, the low stress material (SDR) was tested as well. Again no cracking was found even days after curing.

EXAMPLES 5-14

Table I below lists the cracking time for several low viscosity, high stress composites. A shorter cracking time suggests a quick, and higher stress development. Obviously, the low stress composite stands up by its no crack capability.

It should be pointed out that the test method with the apparatus disclosed herein is effective in visualizing the impact of curing stress and in ranking the materials with a variety of curing stresses. In addition, it was also found that such a setup can also be used to visualize the impact of curing shrinkage if no bond-enhancing process is applied.

TABLE I

| FLOWABLE PRODUCT | Crack Time (sec) | Stress (Mpa) | Shrinkage (%) | Modulus (Mpa) | ISO Depth of Cure (mm) |
|---|---|---|---|---|---|
| Dyract Flow A3 | during cure | >4.2 | 6.0 | 4267 | 2.1 |
| Flow-It A2 | 3" ± 3" | 3.8 | 5.0 | 5089 | — |
| GrandiO Flow A2 | 15" ± 1" | >4.2 | 3.9 | 8173 | 2.8 |
| Filtek Supreme Plus Flow A2 | 25" ± 15" | 3.9 | 4.6 | 5064 | 2.6 |
| Esthet-X Flow A2 | 43" ± 18" | 3.2 | 4.5 | 4637 | 3.3 |
| TPH 3 Flow A2 | 46" ± 30" | 3.1 | 4.5 | 4490 | 3.3 |
| Premise Flow A1 | 60" ± 14" | 3.2 | 3.8 | 5126 | 2.4 |
| Clearfil Majesty Flow A2 | 60" ± 60" | 3.0 | 3.5 | 7706 | 2.6 |
| Tetric Evo Flow A2 | 85" ± 32" | 2.9 | 4.3 | 3994 | 1.8 |
| Tokuyama Estelite Flow Quick A2 | 90" ± 90" | 3.7 | 3.8 | 6517 | 2.4 |
| Surefil SDR Universal Shade | *no crack | 1.5 | 3.6 | 5800 | 4.3 |

*Surefil SDR may cause crack from an hour to days post cure, if at all

Thus, it should be evident that the apparatus and testing method as disclosed herein carries out one or more of the objects set forth above and otherwise constitutes an advantageous contribution to the art. As will be apparent to persons skilled in the art, modifications can be made to the embodiments disclosed herein without departing from the spirit of the disclosure.

What is claimed is:

1. An apparatus for visualizing contraction stress of any curable material during the course of curing or immediately after such a curing process, said apparatus including:
   a sandwich core setup comprising:
      a substrate that is rigid enough to avoid any deformation by the contraction stress of curing;
      a spacer; and
      a cover slip having a thickness of from about 0.01 mm to about 1.00 mm
   a secondary setup to ensure reproducibility comprising:
      a supporting bed configured for holding and centering the substrate;
      a ride-on part configured for support a lid;
      the lid is configured for serving as a light-guide holder; and
      a base configured for stabilizing the supporting bed.

2. The apparatus of claim 1, wherein the substrate many be a pre-cleaned substrate, an untreated substrate, a sand-blasted substrate, a silanated substrate, an etched substrate, or a combination thereof.

3. The apparatus of claim 1, wherein the cover slip has a size of about 24 mm×24 mm and is pre-cleaned.

4. The apparatus of claim 3, wherein the cover slip is sand-blasted substrates with a silane application or etched with a silane application.

5. The apparatus of claim 1, wherein the spaces must includes a top surface having a flat surface and a bottom having a flat surface such that a good contact is present between the substrate and the cover slip.

6. The apparatus of claim 5, wherein the spacer has a thickness of from about 0.10 mm to about 5.0 mm.

7. The apparatus of claim 5, wherein the spacer has an inner diameter of from about 15 mm to about 25 mm and an outer diameter of from about 20 mm to about 30 mm.

8. The apparatus of claim 1, wherein the supporting bed is configured for accommodating the substrate in a centralized and axially aligned orientation.

9. The apparatus of claim 1, wherein the ride-on part includes a single or a dual well such that more than one spacer and cover slip may be utilized in the apparatus.

10. The apparatus of claim 1, wherein the lid includes a circular opening having a diameter of about 7.5 mm such that a tip of standard light guide may be accommodated.

11. The apparatus of claim 1, wherein a gap between a bottom of the lid and a top of the cover slip having the curable material is from about 0.5 mm to about 1.0 mm.

12. A method utilizing an apparatus to visualize a contraction stress during a curing process, the method comprising:
   a. setting substrate on top of a supporting bed that is properly aligned with a base;
   b. setting a spacer on top of the substrate;
   c. placing a lid having at least one well onto the spacer;
   d. applying a curable material onto a cover slip in order to load the cover slip;
   e. inverting the loaded cover slip and setting it on a cert of the spacer;
   f. optionally applying pressure to the loaded cover slip in order to create a contact between the curable material and the substrate;
   g. placing a light guide holder onto the lid while ensuring that a bottom part of the lid does not touch any part of the loaded cover slip;
   h. curing the curable material, and
   i. determining the severity of the contraction stress of the curable material based on an amount of time until the cover slip cracks.

* * * * *